United States Patent [19]

Honda et al.

[11] 4,313,888
[45] Feb. 2, 1982

[54] N-3-(CIS-9-OCTADECENOYLOXY)-2-HYDROXYPROPYLAMINE DERIVATIVE

[75] Inventors: Keiichi Honda, Odawara; Yasushi Nishijima, Kamakura, both of Japan

[73] Assignee: Kanebo Ltd., Tokyo, Japan

[21] Appl. No.: 187,045

[22] Filed: Sep. 15, 1980

[51] Int. Cl.³ .......................... C09F 5/00; B01F 17/30
[52] U.S. Cl. ........................................ 260/404; 252/356
[58] Field of Search .......................... 260/404; 252/356

[56] References Cited

U.S. PATENT DOCUMENTS

| | | | |
|---|---|---|---|
| 1,946,079 | 2/1934 | Kern et al. | 260/404 |
| 2,993,919 | 7/1961 | Findley et al. | 260/404 |
| 3,383,397 | 5/1968 | Milks et al. | 260/404 |
| 3,439,007 | 5/1969 | Milks | 260/404 |

*Primary Examiner*—John F. Niebling
*Attorney, Agent, or Firm*—Armstrong, Nikaido, Marmelstein & Kubovcik

[57] ABSTRACT

A novel N-3-(cis-9-octadecenoyloxy)-2-hydroxypropylamine derivative, useful as a nonionic surface active agent, especially, an emulsifying agent and dispersing agent for cosmetics, is of the general formula:

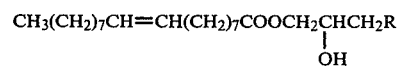

in which R represents a member selected from the group consisting of

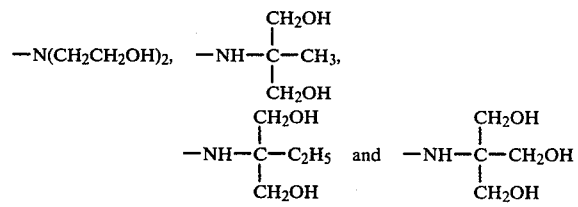

7 Claims, No Drawings

N-3-(CIS-9-OCTADECENOYLOXY)-2-HYDROXY-PROPYLAMINE DERIVATIVE

BACKGROUND OF THE INVENTION

1. Field of the Invention

The present invention relates to novel N-3-(cis-9-octadecenoyloxy)-2-hydroxypropylamine derivative. More particularly, the present invention relates to novel N-3-(cis-9-octadecenoyloxy)-2-hydroxypropylamine derivative which is extremely useful as a nonionic surface active agent, especially an emulsifying agent and a dispersing agent for cosmetics.

2. Description of the Prior Art

It is well known that various nonionic surface-active agents are useful as an emulsifying agent or a dispersing agent for the manufacture of cosmetics or paint compositions, and for emulsion and dispersion polymerization processes. However, it is very difficult to find a nonionic surface-active agent which is suitable for the preparation of a w/o type emulsion and which has all of the advantages of their emulsifying activity and dispersing power (dispersibility for pigments) being excellent, their capability of stably holding water in the form of a w/o type emulsion being excellent, their irritating property to the skin being very poor and their hydienic safty being excellent. For example, polyoxyethylene higher alkyl ethers exhibit a poor emulsifying activity. Accordingly, it is necessary to use the polyoxyethylene higher alkyl ethers in a large amount. Also, in the case of the higher fatty acid esters of polyols (for example, glycerol, sorbitan, polyethylene glycol etc.), the resultant emulsion is frequently gelatinized. Therefore, the emulsion has a poor durability (storage stability). Higher fatty acid esters of alkanol amines (for example, triethanol amine) exhibit unsatisfactory emulsifying and dispersing power. Moreover, higher fatty acid amides of alkanolamines have unsatisfactory emulsifying and dispersing activities, as well as a considerable skin-irritating property, and therefore, the use of said fatty acid amides is limited.

Under the above-mentioned circumstances, the inventors of the present invention carried out a wide range of systematic studies for surface active agents. As a result, it was found that specific novel N-3-(cis-9-octadecenoyloxy)-2-hydroxypropylamine derivative exhibits an excellent surface-activity, a very small irritation effect on human skin and an excellent physiological acceptability. That is, these novel compounds are useful as an emulsifying and dispersing agent for cosmetics as well as pigments, and exhibit an excellent water-emulsifying activity in a w/o type emulsion (water-includible ability).

SUMMARY OF THE INVENTION

An object of the present invention is to provide novel N-3-(cis-9-octadecenoyloxy)-2-hydroxypropylamine derivative useful as a nonionic surface active agent, especially, an emulsifying and dispersing agent.

Another object of the present invention is to provide novel N-3-(cis-9-octadecenoyloxy)-2-hydroxypropylamine derivative which does not irritate human skin.

The N-3-(cis-9-octadecenoyloxy)-2-hydroxypropylamine derivative of the present invention is of the general formula (I):

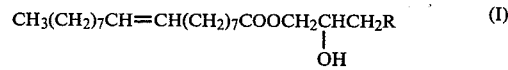

in which R represents a member selected from the group consisting of

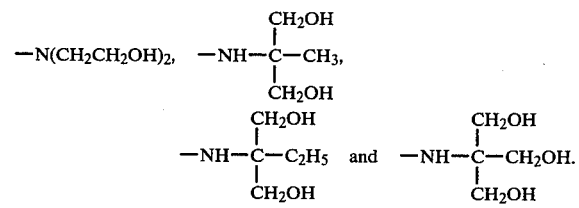

DETAILED DESCRIPTION OF THE PREFERRED EMBODIMENTS

The N-3-(cis-9-octadecenoyloxy)-2-hydroxypropylamine derivative of the present invention having the formula (I) include N-3-(cis-9-octadecenoyloxy)-2-hydroxypropyldiethanolamine, N-3-(cis-9-octadecenoyloxy)-2-hydroxypropyl-2-amino-2-methyl-1,3-propanediol, N-3-(cis-9-octadecenoyloxy)-2-hydroxypropyl-2-amino-2-ethyl-1,3-propanediol, and N-3-(cis-9-octadecenoyloxy)-2-hydroxypropyltrimethylolaminomethane.

Usually, each of the compounds of the present invention can be obtained by a process in which glycidyl oleate directly reacts with diethanolamine, 2-amino-2-methyl-1,3-propanediol, 2-amino-2-ethyl-1,3-propanediol, or trimethylolaminomethane, at an elevated temperature. This process can be easily carried out on an industrial scale, because the above-mentioned addition reaction can be completed at a relatively low temperature within a short time, in spite of the fact that no catalyst is used.

Usually, each compound of the formula (I) is prepared in such a manner that glycidyl oleate is mixed with an alkanolamine as mentioned above in a molar ratio of 1:0.9 to 1:2.2 and, then, the mixture is heated at a temperature of from 70° to 120° C., for 3 to 4 hours, to subject the two compounds to addition reaction.

The isolation of the reaction product from the reaction mixture is usually carried out as follows. After the reaction is completed, a large amount of petroleum ether or ligroin is added to the reaction mixture, and the mixture is stirred. The mixture is allowed to stand, so as to allow non-reacted alkanolamine to precipitate from the mixture. The precipitated alkanolamine is removed from the mixture by means of decantation or filtration. The solvent is distilled away from the petroleum ether solution (or ligroin solution) and the resultant residue is distilled in a high-vacuum. Thereafter, the distilate is refined by means of column chromatography or recrystallization to obtain a purified product. The compounds of the formula (I) of the present invention are in the form of either a viscous colorless or light yellow liquid, or a colorless crystal. The compounds exhibit a poor solubility in water, and excellent solubilities in alcohol, petroleum ether and chloroform et al. In Table 1, specific physical properties of the compounds of the present invention, by which the compounds of the present invention can be identified, are indicated.

TABLE 1

| Compound | M.P. (°C.) | Characteristic Absorption Band in I.R. Spectrum (cm$^{-1}$) | Mass Spectral Data (QM$^+$,CI, isobutane) | Elementary Analysis | |
|---|---|---|---|---|---|
| | | | | Found | Calculated |
| N-3-(cis-9-octadecenyoloxy)-2-hydroxypropyldiethanolamine | — | 3350,2900, 2840,1735, 1455,1165, 1070,1035, and 865, | 660(M$^+$+1) | C:67.59% H:11.17% N:3.15% (Molecular Formula:C$_{25}$H$_{49}$O$_5$N) | (67.68%) (11.13%) (3.16%) |
| N-3-(cis-9-octadecenyoloxy)-2-hydroxypropyl-2-amino-2-methyl-1,3-propanediol | 63 ~ 65 | 3340,2910, 2840,1735, 1460 and 1040, | 660(M$^+$+1) | C:67.61% H:11.16% N:3.17% (Molecular Formula:C$_{25}$H$_{49}$O$_5$N) | (67.68%) (11.13%) (3.16%) |
| N-3-(cis-9-octadecenoyloxy)-2-hydroxypropyltrimethylolaminomethane | 68 ~ 70 | 3340,2910, 2840,1735, 1460 and 1035 | 748(M$^+$+1) | C:65.18% H:10.83% N:3.01% (Molecular Formula:C$_{25}$H$_{49}$O$_6$N) | (65.32%) (10.74%) (3.05%) |
| N-3-(cis-9-octadecenoyloxy)-2-hydroxypropyl-2-amino-2-ethyl-1,3-propanediol | — | 3340,2910, 2840,1735, 1460 and 1040, | 674(M$^+$+1) | C:68.31% H:11.25% N:3.09% (Molecular Formula:C$_{26}$H$_{51}$O$_5$N) | (68.23%) (11.23%) (3.06%) |

The mass spectrum was measured by using a tris- or tetrakis-tri-methyl-silyl(TMS) derivative of each compound.

The above mentioned compounds of the present invention exhibit an extremely poor skin-irritating property. The primary skin-irritating indexes of the compounds (A~D) of the present invention and other compound (E~H), which were determined by using female New Zealand-strain white rabbits, each having a weight of from 2.8 to 3.2 kg, in accordance with the Draize method, are shown in Table 2.

TABLE 2

| Type of Compound | Primary Skin-irritating Index | | | |
|---|---|---|---|---|
| | Concentration of Compound | | | |
| | 0% | 0.2% | 2% | 20% |
| A | 0 | 0 | 0.9 | 1.1 |
| B | 0 | 0 | 0.7 | 1.0 |
| C | 0 | 0 | 0.7 | 1.2 |
| D | 0 | 0 | 0.8 | 1.2 |
| E | 0 | 0.3 | 2.3 | 4.7 |
| F | 0 | 0.3 | 2.8 | 4.6 |
| G | 0 | 1.4 | 5.6 | 7.1 |
| H | 0 | 0.2 | 1.2 | 2.6 |

NOTE:
(1) The compounds A ~ H were the same as those described in Example 5.
(2) Each compound was dissolved in a predetermined concentration in olive oil.
(3) The Draize Method is disclosed in Draize, J. H., Associations of Food and Drug Officials of the United States, "Appraisal of the Safety of Chemicals in Foods, Drugs and Cosmetics", 46 (1959), Texas, State Department of Health, Austin.

The compounds of the formula (I) of the present invention possess an excellent surface activity and are very useful as an emulsifying agent, dispersing agent, or an intermediate of a cationic surface active agent, anionic surface active agent and amphoteric surface active agent. In the case where the compounds of the present invention are used as an emulsifying agent for manufacturing water-in-oil (w/o) type emulsions (for example, vinyl type polymer emulsions, w/o emulsion type cosmetics such as milky lotions and creams), the compounds exhibit very special effects. For example, they reveal very excellent emulsifying activity and water-inclusive activity in w/o type emulsion, which are never attained by conventional homologous compounds such as N-3-(cis-9-octadecenoyloxy)-2-hydroxypropyldiethylamine, N-3-(cis-9-octadecenoyloxy)-2-hydroxypropyltert.butylamine, cis-9-octadecenoic acid diethanolamide, cis-9-octadecenoic acid-1,1-dimethylethylamide, cis-9-octadecenoic acid trimethylmethylamide.

Accordingly, the compound of the present invention is effective for preparing w/o type emulsions having an excellent storage stability, resistance to change in the temperature thereof and uniformity. Also, the compound of the present invention exhibit a more excellent dispersing activity for various pigments, for example, carbonblack, than that of the above-mentioned conventional homologous compounds. Furthermore, the compounds of the present invention are very useful as a dispersing agent for paint compounds.

The specific examples presented below will serve to more fully elaborate how the present invention is practiced. However, it should be understood that the examples are only illustrative and in no way limit the present invention. In the examples, all percentages and parts are based on weight.

EXAMPLE 1

Preparation of N-3-(cis-9-octadecenoyloxy)-2-hydroxypropyldiethanolamine

A 200 ml flask with a stirrer was charged with a mixture of 25 g of diethanolamine and 50 g of glycidyl oleate. The mixture was heated at 70° C., for 4 hours, while vigorously stirring it, so as to complete the addition reaction of diethanolamine with glycidyl oleate. After the reaction was completed, the reaction mixture was cooled to room temperature and mixed with 100 ml of petroleum ether. The mixture was stirred and, then, allowed to stand for about 2 hours. The precipitated non-reacted diethanolamine was removed from the reaction mixture by means of decantation and the supernant solution was condensed under a reduced pressure. The condensed solution was distilled under a high vacuum (70 m Torr) to provide a distillation fraction at a temperature of from 150° to 180° C. The distillation fraction was refined by a column chromatography, in which a silica gel was used as a packing and a aceton/chloroform/n-hexane (50/30/20 v/v%) mix was used as an eluent. 57 g (which corresponds to 87% of the theoretical yield) of a viscous light yellow liquid were obtained. The resultant light yellow liquid was subjected to measurements of the IR spectrum, mass spectrum and melting points thereof, and to an elementary analysis thereof. As a result, it was confirmed that the resultant liquid consisted of N-3-(cis-9-octadecenoyloxy)-2-hydroxypropyldiethanolamine. In the measurement of the mass spectrum, the resultant liquid compound was converted into its TMS-derivative.

EXAMPLE 2

Preparation of
N-3-(cis-9-octadecenoyloxy)-2-hydroxypropyl-2-amino-2-methyl-1,3-propanediol The same flask as that mentioned in Example 1, was charged with a mixture of 25 g of 2-amino-2-methyl-1,3-propanediol and 50 g of glycidyl oleate. The mixture was heated at 110° C., for 4 hours, while vigorously stirring it. After the reaction was completed, the reaction mixture was subjected to the same procedures (decantation, condensation, vacuum distillation) as described in Example 1. A pasty light yellow material was obtained. Then, the resultant material was recrystallized twice from acetone. The recrystallized product was 55.7 g (which corresponds to 85% of theoretical yield) of colorless crystals. The resultant colorless crystals were subjected to measurements of the IR spectrum, mass spectrum and melting points thereof, and to an elementary analysis thereof. As a result, it was confirmed that the resultant crystals consisted of N-3-(cis-9-octadecenoyloxy)-2-hydroxypropyl-2-amino-2-methyl-1,3-propanediol having high purity. In the measurement of the mass spectrum, the resultant compound was converted into its TMS-derivative.

EXAMPLE 3

Preparation of
N-3-(cis-9-octadecenoyloxy)-2-hydroxypropyl-2-amino-2-ethyl-1,3-propanediol The same flask at that mentioned in Example 1, was charged with a mixture of 25 g of 2-amino-2-ethyl-1,3-propanediol and 50 g of glycidyl oleate. The mixture was heated at 70° C., for 4 hours, while vigorously stirring it. After the reaction was completed, the reaction mixture was cooled to room temperature and subjected to the same procedures (decantation, condensation, vacuum distillation) as described in Example 1. A visous light yellow material was obtained. The resultant product was 58 g (which corresponds to 58.9% of theoretical yield) of visous liquid.

The resultant viscous liquid was subjected to measurements of the IR spectrum, mass spectrum, gas chromatography and melting points thereof, and to an elementary analysis thereof. As a result, it was confirmed that the resultant liquid consisted of N-3-(cis-9-octadecenoyloxy)-2-hydroxypropyl-2-amino-2-ethyl-1,3-propanediol. In the measurement of the mass spectrum and gas chromatography, the resultant liquid compound was converted into its TMS-derivative.

EXAMPLE 4

Preparation of
N-3-(cis-9-octadecenoyloxy)-2-hydroxypropyltrimethylolaminomethane The same flask as that mentioned in Example 1, was charged with a mixture of 25 g of trimethylolaminomethane and 50 g of glycidyl oleate. The mixture was heated at 120° C., for 4 hours, while vigorously stirring it. After the reaction was completed, the reaction mixture was cooled to room temperature and subjected to the same procedures (decantation, condensation, vacuum distillation) as described in Example 1. A semisolid light yellow material was obtained. Then, the resultant material was recrystallized twice from acetone. The recrystallized product was 59 g (which corresponds to 87% of theoretical yield) of colorless crystals. The resultant colorless crystals were subjected to measurements of the IR spectrum, mass spectrum, gas chromatography and melting points thereof, and to an elementary analysis thereof. As a result, it was confirmed that the resultant crystals consisted of N-3-(cis-9-octadecenoyloxy)-2-hydroxypropyltrimethylolaminomethane. In the measurement of the mass spectrum and gas chromatography, the resultant colorless crystals were converted into their TMS-derivative.

EXAMPLE 5

Application of the Compounds of the Present Invention as a Emulsifying Agent

Each of the compounds A through D of the present invention and comparative compounds E through H were used as an emulsifying agent.

| | Compound |
|---|---|
| A | N-3-(cis-9-octadecenoyloxy)-2-hydroxypropyl-diethanolamine |
| B | N-3-(cis-9-octadecenoyloxy)-2-hydroxypropyl-2-amino-2-methyl-1,3-propanediol |
| C | N-3-(cis-9-octadecenoyloxy)-2-hydroxypropyl-2-amino-2-ethyl-1,3-propanediol |
| D | N-3-(cis-9-octadecenoyloxy)-2-hydroxypropyl trimethylolaminomethane |
| E | N-3-(cis-9-octadecenoyloxy)-2-hydroxypropyl diethylamine |
| F | N-3-(cis-9-octadecenoyloxy)-2-hydroxypropyl tert. butylamine |
| G | cis-9-octadecenoic acid diethanolamide |
| H | sorbitansesquioleate |

5 parts by weight of each compound were mixed with 30 parts by weight of liquid paraffin. The mixture was heated to 70° C., and mixed with 65 parts of hot water having a temperature of 70° C., while vigorously stirring the mixture, so as to disperse and emulsify the water. The resultant emulsion was slowly cooled to a temperature of 30° C., while gently stirring it to form a w/o type emulsion. The emulsion was diluted with liquid paraffin at a diluting ratio of 1:2000. The diluted emulsion was subjected to the measurement of the light absorbance thereof at 450 nm. The results are indicated in Table 3. In Table 3, the light absorbance of a sorbitansesquioleate(H) containing emulsion is expressed as 100, and the light absorbance of each of the other emulsions is expressed by a relative value thereof to that of the sorbitansesquioleate(H) containing emulsion.

TABLE 3

| Compound | Light Absorbance |
|---|---|
| A | 128 |
| B | 124 |
| C | 120 |
| D | 223 |
| E | 73 |
| F | 65 |
| G | 80 |
| H | 100 |

It is known that, generally, when the size of emulsified particles is within a certain range, the smaller the size of the particles in the emulsion, the higher the light absorbance of the emulsion. As is clear from Table 3, the emulsions containing each of the compounds (A, B, C and D) of the present invention possess a higher light absorbance than those of the comparative compounds. Also, when the emulsions were observed by means of a microscope, it was found that the compounds of the present invention were more effective for forming emulsions in which the emulsified particles are very small than the comparative compounds. Consequently, it is evident that the compounds of the present invention are very useful as an emulsifying agent, especially, for preparing the w/o type emulsions.

EXAMPLE 6

Application of the Compounds of the Present Invention as an Emulsifying Agent for Preparing an Acrylic Type Resin Aqueous Emulsion As an agent, 50 parts by weight of each of the compounds, A, B, C, and D of the present invention and the comparative compounds E, F, G and H were mixed with 350 parts by weight of heavy oil and 150 parts by weight of methyl methacrylate, 60 parts by weight of ethyl acrylate. Then, the mixture was further mixed with 400 parts by weight of water, at a temperature of 60° C., while stirring the mixture, to provide an aqueous emulsion.

To this mixture was added 0.25 parts by weight of azobisisobutyronitrile as a polymerization initiator. The resultant mixture was subjected to an emulsion polymerization process at a temperature of 60° C., for 2.5 hours, to prepare a w/o type emulsion of a methylmethacrylate-ethylacrylate copolymer. Each emulsion was allowed to stand in an air-conditioned chamber at a temperature of 45° C., for 12 months, to test the storage-stability of the emulsion.

As a result of the storage-stability test, it was observed that the emulsion containing the compounds A, B, C or D of the present invention as an emulsifying agent, contained uniform, very fine particles of the copolymer and no change in the emulsion was found even 12 months after the storage of the emulsion. However, in the case of the emulsion containing, as an emulsifying agent, the compounds E, F, G or H, the particles of the copolymer were coarse. In the emulsion containing the compound H, the heavy oil was separated from the emulsions after one month storage, and water was separated from the remaining emulsion after three-months storage. Also, in the case of the emulsion containing the comparative compounds E, F or G, the heavy oil was separated from the emulsion after storing it for 10 days and, therefore, water was separated from the remaining emulsion after storing it for three months.

From the results of the above-mentioned storing test, it is clear that the emulsions containing the compounds of the present invention is superior in emulsifying activity and stability for storage than the emulsions containing the comparative compounds.

Therefore, the compounds (A, B, C and D) of the present invention are extremely useful as an emulsifying agent for the production of an acrylic polymer emulsion by emulsion polymerizing an acrylic monomer.

EXAMPLE 7

Application of the Compounds of the Present Invention for Dispersing Pigments

One part by weight of a dispersing agent consisting of one member selected from the compounds A, B, C and D and the comparative compounds E, F, G and H, was dissolved in 78 parts by weight of a liquid paraffin (heavy oil). One part by weight of finely pulverized titanium dioxide (the particles of which had an average size of 30 mμ) was mixed with the above-mentioned solution, while vigorously stirring the mixture at room temperature, to prepare a uniform dispersion. The dispersion was allowed to stand at room temperature for 20 hours. Thereafter, 0.5 part by weight of a supernatant portion was skimmed from the emulsion. The supernatant liquid was diluted with the same liquid paraffin as stated above, to provide a diluted dispersion having a volume corresponding to 100 times the original volume of the supernatant liquid.

The diluted dispersion was subjected to a light absorbance measurement at a length of 300 nm. The results of the measurement are indicated in Table 4. The data in Table 4 is expressed by conversion data in which sorbitansesquioleate(H) is 100.

TABLE 4

| compound | Absorbance |
| --- | --- |
| A | 134 |
| B | 200 |
| C | 141 |
| D | 146 |
| E | 87 |
| F | 72 |
| G | 89 |
| H | 100 |

In view of Table 4, it is obvious that the compounds (A, B, C and D) of the present invention exhibited more excellent dispersing activity than that of the comparative compounds (E, F, G and H). As a result of another experiment, it was formed that the compounds of the present invention are more effective for dispersing other pigments than the comparative compounds. Furthermore, it was found that the compounds of the present invention are effective as a dispersing agent for various pigments in coating compositions.

EXAMPLE 8

Application of the Compounds of the Present Invention as an Emulsifying Agent

A solution was prepared by dissolving 5 parts by weight of one member selected from the compounds A, B, C and D of the present invention or the comparative compounds E, F, G and H in 35 parts by weight of liquid paraffin. Thereafter, 60 parts by weight of water were gradually mixed to the solution at a temperature of 20° C. while stirring it to prepare a w/o type aqueous emulsion.

The stability for storing of the resultant emulsion was determined by detecting the separation of the liquid paraffin from the emulsion. The results are indicated in Table 5.

The stability of the emulsion was measured in the following manner. The initial volume (A) of the emulsion just after the preparation thereof was measured. After storing the emulsion for a predetermined period of time, when some compornents were separated from the emulsion, the volume (B) of the remaining emulsion was measured. The stability of the emulsion after the storage of the predetermined period was expressed by a ratio of B/A in percent.

TABLE 5

| Compound | Stability of emulsion storage period | | |
|---|---|---|---|
| | 48 hours | 7 days | 3 months |
| A | 100 | 99.4 | 95.6 |
| B | 100 | 100 | 95.9 |
| C | 100 | 99.1 | 95.1 |
| D | 100 | 99.5 | 95.3 |
| E | 0 | — | — |
| F | 0 | — | — |
| G | 82.0 | 0 | — |
| H | 97.6 | 91.0 | 82.7 |

As is obvious from the results indicated in Table 5, the compounds A, B, C and D of the present invention were more effective for preparing a stable, uniform w/o type emulsion than the comparative compounds E, F, G and H.

EXAMPLE 9

Application of the Compounds of the Present Invention as an Emulsifying Agent

Eight types of w/o type creams were prepared by separately using, an an emulsifying agent, each of the compounds A, B, C and D of the present invention and the comparative compounds E, F, G and H in accordance with the following procedures.

10 parts by weight of liquid paraffin were mixed with 2 parts by weight of microcrystalline wax, 2 parts by weight of lanolin, 3 parts by weight of octyldodecanyl myristate, 0.1 part by weight of butyl p-hydroxybenzoate and 0.1 part by weight of the above-mentioned emulsifying agent. The resultant mixture was heated to a temperature of 80° C. to melt it. Thereafter, a mixture of 8 parts by weight of a 70% sorbitol aqueous solution, 0.1 part by weight of methyl p-hydroxybenzoate, 0.3 part by weight of a perfume and 70.5 parts by weights of water were gradually added to the melt, while stirring the mixture, to prepare a uniform emulsion. Thereafter, the emulsion was gradually cooled to room temperature, while stirring it, to provide a w/o type cream. The w/o type cream was stored in a constant temperature chamber maintained at 45° C., for a predetermined period of time, to test the stability of the cream for storage. The stability of the cream was evaluated by the same method as that described in Example 8. The results are indicated in Table 6

TABLE 6

| Compound | Stability of cream Storage Period | | |
|---|---|---|---|
| | one week | one month | one year |
| A | 100 | 100 | 100 |
| B | 100 | 100 | 100 |
| C | 100 | 100 | 100 |
| D | 100 | 100 | 100 |
| E | 0 | — | — |
| F | 0 | — | — |
| G | 92.1 | 73.0 | 0 |
| H | 97.3 | 88.4 | 74.2 |

As is obvious from the results indicated in Table 6, the compounds A, B, C and D of the present invention were more effective for preparing a highly stable w/o type emulsion than the compounds E, F, G and H. Before the present invention, it was impossible to prepare a w/o type cream and milky lotion containing stably emulsified water in an amount of 60% or more, by using sorbitansesquioleate (compound H) as an emulsifying agent for the w/o type emulsion. However, with the compounds of the present invention, it became possible to easily provide a very stable w/o type cream or milky lotion containing 60% by weight or more of the emulsified water.

From the Examples 5 through 9, it is evident that the compounds of the present invention exhibit a more excellent emulsifying, dispersing and water-retaining activity in the preparation of virious types of w/o type emulsions, than those of the conventional emulsifiers.

We claim:

1. A N-3-(cis-9-octadecenoyloxy)-2-hydroxypropylamine derivative of the general formula (I):

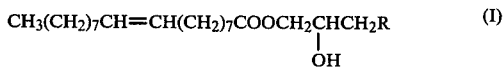

wherein R represents a member selected from the group consisting of

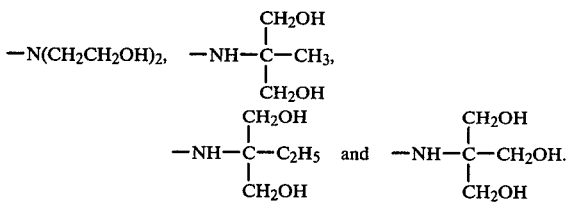

2. The derivative of claim 1, which is N-3-(cis-9-octadecenoyloxy)-2-hydroxypropyldiethanolamine.

3. The derivative of claim 1, which is N-3-(cis-9-octadecenoyloxy)-2-hydroxypropyl-2-amino-2-methyl-1,3-propanediol.

4. The derivative of claim 1, which is N-3-(cis-9-octadecenoyloxy)-2-hydroxypropyl-2-amino-2-ethyl-1,3-propanediol.

5. The derivative of claim 1, which is N-3-(cis-9-octadecenoyloxy)-2-hydroxypropyltrimethylolaminomethane.

6. An emulsifying agent comprising at least one N-3-(cis-9-octadecenoyloxy)-2-hydroxypropylamine derivative of the general formula (I):

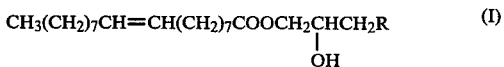

wherein R represents a member selected from the group consisting of

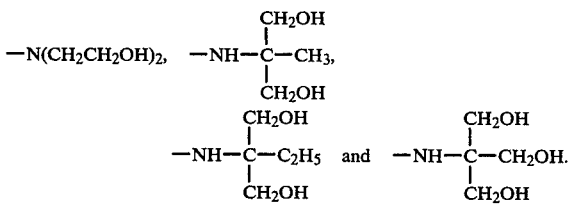

7. A dispersing agent comprising at least one N-3-(cis-9-octadecenoyloxy)-2-hydroxypropylamine derivative of the general formula (I):

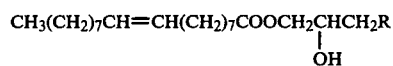　(I)
wherein R represents a member selected from the group consisting of
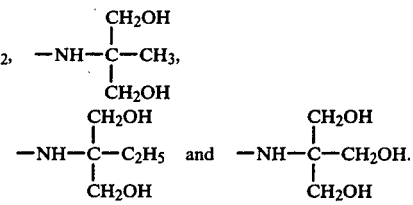
* * * * *